(12) United States Patent
LaVay et al.

(10) Patent No.: US 7,344,708 B1
(45) Date of Patent: Mar. 18, 2008

(54) SILICONE POLYESTER RESINS

(75) Inventors: Carter LaVay, Riverside, CT (US);
Anthony J. O'Lenick, Jr., Dacula, GA (US)

(73) Assignee: Zenitech LLC, Old Greewich, CT (US)

( * ) Notice: Subject to any disclaimer, the term of this patent is extended or adjusted under 35 U.S.C. 154(b) by 601 days.

(21) Appl. No.: 10/989,822

(22) Filed: Nov. 17, 2004

(51) Int. Cl.
*A61Q 5/12* (2006.01)

(52) U.S. Cl. ............... 424/70.12; 556/437; 556/441
(58) Field of Classification Search ............ None
See application file for complete search history.

(56) References Cited

U.S. PATENT DOCUMENTS

| 4,724,248 A | 2/1988 | Dexter et al. |
| 5,136,063 A | 8/1992 | O'Lenick, Jr. |
| 5,210,133 A | 5/1993 | O'Lenick, Jr. |
| 5,411,729 A | 5/1995 | O'Lenick, Jr. |
| 5,475,125 A | 12/1995 | O'Lenick, Jr. |
| 6,972,123 B1 * | 12/2005 | O'Lenick, Jr. ........... 424/78.02 |

* cited by examiner

*Primary Examiner*—Michael Woodward
*Assistant Examiner*—Bethany Barham

(57) ABSTRACT

The present invention relates to a series of novel silicone polyesters which are prepared by crosslinking a dimethicone copolyol having at least 4 hydroxyl groups with a dimer acid. The ratio of acid groups to hydroxyl groups ranges from 0.7 to 1.4 so that a significant number of groups are reacted and a significant number of crosslink groups are achieved.

20 Claims, No Drawings

SILICONE POLYESTER RESINS

BACKGROUND OF THE INVENTION

1. Field of the Invention

The present invention relates to a series of novel silicone polyesters which are prepared by crosslinking a dimethicone copolyol having at least 4 hydroxyl groups with a dimer acid. The ratio of acid groups to hydroxyl groups ranges from 0.7 to 1.4 so that a significant number of groups are reacted and a significant number of crosslink groups are achieved.

2. Arts and Practices

A number of silicone esters are known in the art. The oldest of them is U.S. Pat. No. 4,724,248 issued Feb. 9, 1988 to Dexter, et al. This patent incorporated herein by reference, teaches that "esters and urethanes of certain polydialkylsiloxanepoly oxyalkylene block and graft copolymers which impart high voltage stabilization to dielectric olefin polymers, the stabilized olefin polymer insulating materials resulting therefrom and electric wire or cable insulated therewith".

Another early patent is U.S. Pat. No. 5,136,063 issued Aug. 4, 1992 to issued O'Lenick, Jr. This patent incorporated herein by reference teaches "the invention relates to a series of novel silicone fatty esters. This class of compounds, provides outstanding softening and lubricating when applied to textiles and fibers. The compounds of the present invention are prepared by reacting a the hydroxyl group in a silicone polymer with a fatty carboxylic acid, ester or anhydride". The product is an ester not a polyester.

Another patent is U.S. Pat. No. 5,210,133 issued May 11, 1993 likewise to O'Lenick, Jr. entitled Silicone polyester polymers as delivery systems. This patent incorporated herein by reference teaches "the invention discloses novel series of silicone polyesters which are useful as delivery systems for a variety of hydroxyl containing active such as lanolin, cholesterol, dihydrocholesterol, Vitamin A, Vitamin D-2, Vitamin D-3, Vitamin D-4, Vitamin E, and Panthenol. Compounds of the invention by are prepared by the esterification of (a) a hydroxyl containing silicone compound selected from silanol and dimethicone copolyol (b) a diacid and (c) a hydroxyl functional active selected from lanolin, cholesterol, dihydrocholesterol, Vitamin A, Vitamin D-2, Vitamin D-3, Vitamin D-4, Vitamin E, and Panthenol; and optionally (d) a mono functional fatty acid. The polyesters of the present invention allow for the formulation of personal care products in which the "active" can be formulated into a variety of solvents without the loss of activity." This patent teaches polyesters, but they are capes with hydroxy functional vitamins. They are not resins (i.e. heavily crosslinked).

Still another patent is U.S. Pat. No. 5,411,729 issued May 2, 1995 likewise to O'Lenick, Jr, covers silicone polyester polymers as durable humectants. This patent incorporated herein by reference, teaches "The invention discloses novel series of silicone polyesters which are useful as humectants for softening, conditioning and lubricating hair and skin. Compounds of the invention by are prepared by the esterification of (a) a hydroxyl containing silicone compound selected from silanol and dimethicone copolyol (b) a diacid and (c) a poly-hydroxy compound selected from the group consisting of glycerin, methyl glycoside, sorbitol and their alkoxylates and (d) optionally a fatty acid. The polyesters of the present invention allow for the formulation of personal care products in which the humectant is substantive to the hair and skin by virtue of the structure of the polyester and can be formulated into a variety of products for delivery to hair and skin." As in the '133 case above the patent covers polyesters, this time capped with water soluble humectant groups.

U.S. Pat. No. 5,475,125 issued Dec. 12, 1995 to O'Lenick, Jr entitled Silicone polyester emulsifiers is likewise incorporated herein by reference, states "The invention discloses novel polyester emulsifiers. Compounds of the invention are made by reacting (a) a dimethicone copolyol, (b) a diacid and (c) a fatty alcohol alkoxylate containing 4 to 20 carbon atoms. The compounds of the invention by virtue of (a) the silicone group, (b) the fatty alcohol terminal group and (c) the polyoxyalkylene present in the compound are extremely efficient emulsifiers for a variety of oils at heretofore unknown levels." While drawn to polyesters, it also includes capping materials.

None of the references understood that polyesters in which there is no capping material, over four hydroxyl groups on the silicone and the correct ratio of hydroxyl to acid result in highly crosslinked resins that provide a coating from aqueous solution to hair, skin and fibers.

THE INVENTION

Object of the Invention

It is the object of the present invention to provide novel highly crosslinked silicone polyester compound which deposit on fibrous materials from aqueous systems. The key to the deposition is the crosslink density, which has been heretofore not understood. The omission of a essential element, the capper from all the old patents and the selection of the proper hydroxy silicone (one having over 4 hydroxyl groups) and the selection of the proper ratio of hydroxyl to carboxyl all allow for products with heretofore unknown efficiency of deposition on substrates.

While not wanting to be limited to a specific theory of the improved deposition, the molecular size and crosslink density results in a high molecular weight product which when placed into water disrupts many hydrogen bonds. This disruption results in the lowest free energy of the system being when the polymer, albeit soluble in water, is out of solution. The fewest hydrogen bonds between water molecules are disrupted when the polymer is absent. This is exactly the phenomenon which occurs when oil floats on water.

SUMMARY OF THE INVENTION

The present invention relates to novel silicone polyester compounds having a high crosslink density and enough ethylene or propylene oxide to be water dispersible. This combination of properties makes the compounds outstanding conditioners and deliverable from dilute aqueous solution.

The compounds of this invention are made by the esterification of dimer acid ester, and a silicone compound having multiple hydroxy functionalities on the molecule. The silicone molecule also has between 40 and 80% ethylene oxide in the molecule to render it water dispersible.

The compounds of the present invention are made by the reaction of Dimer acid with specific dimethicone copolyol at very specific ratios of hydroxyl to carboxy (acid) groups.

The present invention teaches a polyester made by the reaction of (a) dimer acid conforming to the following structure:

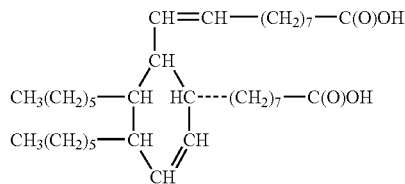

or hydrogenated dimer acid conforming to the following structure:

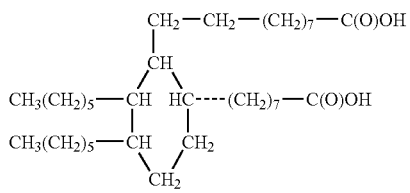

or mixtures thereof;

with (b) a dimethicone copolyol conforming to the following structure:

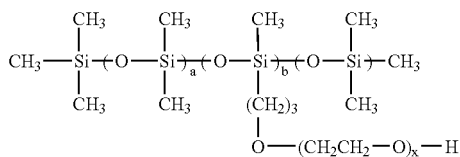

wherein:

a is an integer ranking from 0 to 100;

b is an integer ranging from 4 to 20, with the proviso that b is greater than or equal to a times 0.75);

x is an integer ranging from 6 to 20;

with the proviso that the ratio of hydroxyl group to hydroxyl group be between 0.7 and 1.4.

The various requirements for the compound above are critical to functionality. (a) The proviso that the ratio of hydroxyl group to acid group be between 0.7 and 1.4, results in a product in which most of the hydroxyl groups will be reacted to crosslink. (b) the proviso that b is greater than or equal to a times 0.75 results in a product that is water dispersible or soluble. (c) The x value being limited to integer ranging from 6 to 20 insures the molecule will be water dispersible or soluble. All of these requirements result in a functional molecule which has been heretofore elusive and highly desirable.

The present invention teaches a process for conditioning hair skin and fiber which comprises contacting the hair skin of fiber with an effective conditioning concentration of a polyester made by the reaction of (a) dimer acid conforming to the following structure:

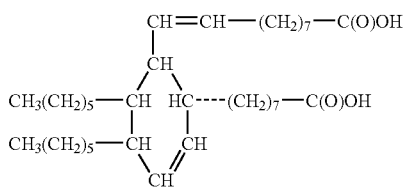

or hydrogenated dimer acid conforming to the following structure:

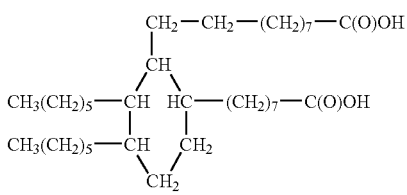

or mixtures thereof;

with (b) a dimethicone copolyol conforming to the following structure:

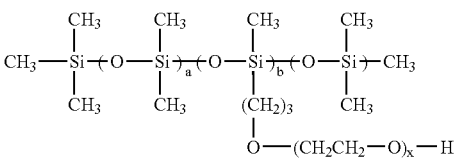

wherein:

a is an integer ranking from 0 to 100;

b is an integer ranging from 4 to 20, with the proviso that b is greater than or equal to a times 0.75);

x is an integer ranging from 6 to 20;

with the proviso that the ratio of hydroxyl group to acid group be between 0.7 and 1.4.

The process is highly efficient since the polyester has been carefully chosen to be crosslinked and water dispersible or soluble. The result is the effective conditioning of hair in anionic systems at concentrations as low as 0.5% by weight.

PREFERRED EMBODIMENTS

In a preferred embodiment x is 10-15.

In another preferred embodiment x is 8-12.

In a preferred embodiment a is 0 to 20.

In a preferred embodiment a is 0.

In a preferred embodiment the ratio of hydroxyl to acid is 1:1.

In another preferred embodiment the ratio of hydroxyl to acid is 1:1.4.

EXAMPLES

Example 1 Dimer Acid

Dimer acid is an item of commerce and is available from a variety of sources including Cognis Chemical Cincinnati Ohio. It conforms to the following structure:

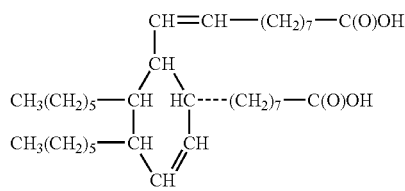

Example 2 Hydrogenated Dimer

Hydrogenated dimer acid is an item of commerce and is available from a variety of sources including Cognis Chemical Cincinnati Ohio. It conforms to the following structure:

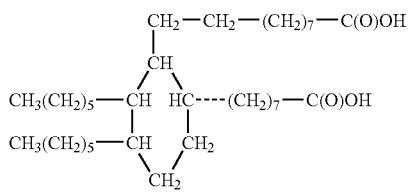

or mixtures thereof;

Dimethicone Copolyol Examples 3-10

The dimethicone copolyol compounds of the present invention are items of commerce and are available from Siltech LLC of Dacula, Ga. They conform to the following structure:

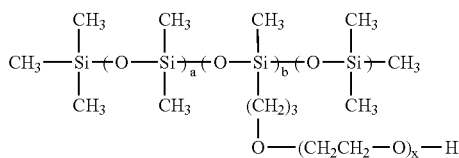

a is an integer ranking from 0 to 100;
b is an integer ranging from 4 to 20, with the proviso that b is greater than or equal to a times 0.75);
x is an integer ranging from 6 to 20;

| Example | a | b | x |
|---------|-----|-----|-----|
| 3 | 0 | 4 | 10 |
| 4 | 10 | 8 | 10 |
| 5 | 15 | 15 | 20 |
| 6 | 20 | 16 | 8 |
| 7 | 100 | 70 | 6 |
| 8 | 20 | 18 | 10 |
| 9 | 5 | 4 | 15 |
| 10 | 10 | 8 | 10 |

General Reaction Conditions

The esterification can be carried out without catalyst; however, when no catalysts are used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

Example 11-26

Into a suitable round bottom, three neck flask equipped with a Dean Stark trap, a thermometer and a nitrogen sparge is added the 150.0 grams of dimer material (Example 1, 2 or mixtures thereof), the specified number of grams of the specified dimethicone copolyol (example 3-10). Next is added 0.25% by weight of the total batch charged of stannous oxylate. The reaction mass is blanketed with nitrogen, and heated to 180° C. and 200° C. under an inert nitrogen blanket. Once the reaction temperature reaches 120° C., water begins to boil off and is collected in the Dean Stark Trap. Within five to ten hours the theoretical water is collected off and the acid value is very low. The product is a clear liquid and is used without additional purification.

| EXAMPLES | Dimer Acid Example | Dimethicone Example | Copolyol Grams | Ratio OH/Acid |
|---------|-----|-----|-----|-----|
| 11 | 1 | 3 | 540.0 | 1:1 |
| 12 | 1 | 4 | 582.0 | 1:1 |
| 13 | 1 | 5 | 980.0 | 1:1 |
| 14 | 1 | 6 | 469.0 | 1:1 |
| 15 | 1 | 7 | 375.0 | 1:1 |
| 16 | 1 | 8 | 680.6 | 1:1 |
| 17 | 1 | 9 | 1065.8 | 1.4:1.0 |
| 18 | 1 | 10 | 728.1 | 1.4:1.0 |
| 19 | 2 | 3 | 432.0 | 1.4:1.0 |
| 20 | 2 | 4 | 466.0 | 0.8:1.0 |
| 21 | 2 | 5 | 784.0 | 0.8:1.0 |
| 22 | 2 | 6 | 375.0 | 0.8:1.0 |
| 23 | 2 | 7 | 300.3 | 0.8:1.0 |
| 24 | 2 | 8 | 435.6 | 0.8:1.0 |
| 25 | 2 | 9 | 852.5 | 0.8:1.0 |
| 26 | 2 | 10 | 582.5 | 1.0:1.0 |

The compounds are yellow viscous liquids and are used without additional purification.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:
1. A polyester made by esterification reaction consisting of reacting:
 (a) a dimer acid source selected from
  dimer acid conforming to the following structure:

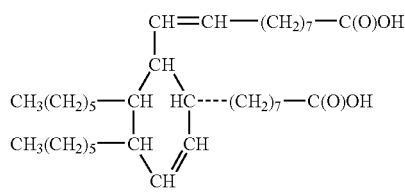

or hydrogenated dimer acid conforming to the following structure:

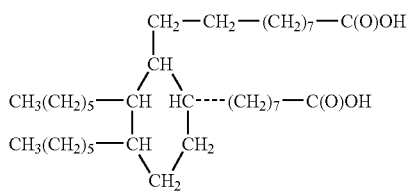

or mixtures thereof;
 with
 (b) a dimethicone copolyol conforming to the following structure:

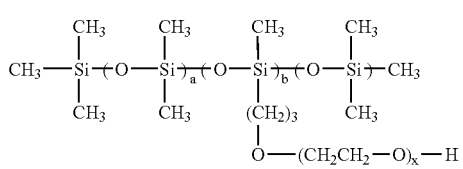

wherein:
a is an integer ranking from 0 to 100;
b is an integer ranging from 4 to 20, with the proviso that b is greater than or equal to a times 0.75);
x is an integer ranging from 6 to 20;
with the proviso that the ratio of hydroxyl group to hydroxyl group be between 0.7 and 1.4.

2. A polyester of claim 1 wherein said esterification reaction is conducted at a temperature of between 120 and 200° C. for five to 10 hours.
3. A polyester of claim 1 wherein said dimer acid source is dimer acid.
4. A polyester of claim 1 wherein said dimer acid source is hydrogenated dimer acid.
5. A polyester of claim 1 wherein x is 10-15.
6. A polyester of claim 1 wherein x is 8-12.
7. A polyester of claim 1 wherein a is 0 to 20.
8. A polyester of claim 1 wherein a is 0.
9. A polyester of claim 1 wherein the ratio of hydroxyl to acid is 1:1.
10. A polyester of claim 1 wherein the ratio of hydroxyl to acid is 1:1.4.
11. A process for conditioning hair skin and fiber which comprises contacting the hair skin of fiber with an effective conditioning concentration of a polyester consisting of the reaction of:
 (a) a dimer acid source selected from
  dimer acid conforming to the following structure:

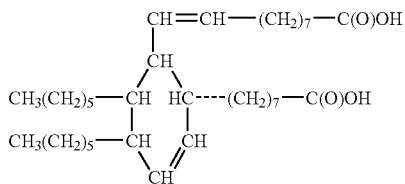

or hydrogenated dimer acid conforming to the following structure:

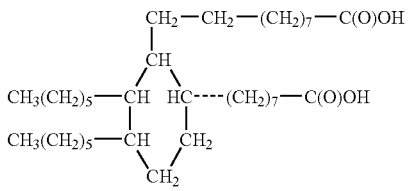

or mixtures thereof;
 with
 (b) a dimethicone copolyol conforming to the following structure:

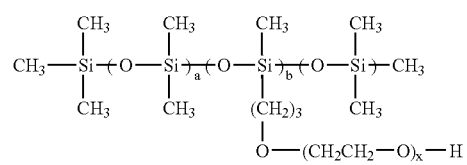

wherein:
a is an integer ranking from 0 to 100;
b is an integer ranging from 4 to 20, with the proviso that b is greater than or equal to a times 0.75);
x is an integer ranging from 6 to 20;
with the proviso that the ratio of hydroxyl group to acid group be between 0.7 and 1.4.

12. A process of claim 11 wherein said effective conditioning concentration ranges between 0.1 and 10% by weight.
13. A process of claim 11 wherein said dimer acid source is dimer acid.
14. A process of claim 11 wherein said dimer acid source is hydrogenated dimer acid.
15. A process of claim 11 wherein x is 10-15.
16. A process of claim 11 wherein x is 8-12.
17. A process of claim 11 wherein a is 0 to 20.
18. A process of claim 11 wherein a is 0.
19. A process of claim 11 wherein the ratio of hydroxyl to acid is 1:1.
20. A process of claim 11 wherein the ratio of hydroxyl to acid is 1:1.4.

* * * * *